(12) United States Patent
Rothbart

(10) Patent No.: US 6,412,198 B1
(45) Date of Patent: *Jul. 2, 2002

(54) FOREFOOT SUPPORT SYSTEM FOR HIGH HEEL SHOES

(75) Inventor: Brian A. Rothbart, St. Petersburg, FL (US)

(73) Assignee: GRD Biotech, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/653,443

(22) Filed: Sep. 1, 2000

Related U.S. Application Data

(63) Continuation-in-part of application No. 09/413,042, filed on Oct. 6, 1999, now Pat. No. 6,212,723, which is a continuation of application No. 09/031,258, filed on Feb. 26, 1998, now Pat. No. 6,092,314, which is a continuation-in-part of application No. 08/733,116, filed on Oct. 16, 1996, now abandoned.

(51) Int. Cl.⁷ .............................. A61F 5/14; A43B 13/12
(52) U.S. Cl. ........................... 36/144; 36/140; 36/30 R; 36/166; 36/180
(58) Field of Search ................................. 36/30 R, 140, 36/143, 144, 166, 169, 172, 180, 181

(56) References Cited

U.S. PATENT DOCUMENTS

| | | |
|---|---|---|
| 353,910 A | 12/1886 | Zacharie |
| 679,947 A | 8/1901 | Collins |
| 841,732 A | 1/1907 | Smith |
| 1,039,396 A | 9/1912 | Hilgert |
| 1,554,883 A | 9/1925 | Sahlin |
| 1,617,132 A | 2/1927 | Morin |

(List continued on next page.)

FOREIGN PATENT DOCUMENTS

| | | |
|---|---|---|
| CH | 241398 | 7/1946 |
| DE | 288914 | 6/1914 |
| FR | 1111706 | 3/1956 |
| FR | 2652260 | 3/1991 |

OTHER PUBLICATIONS

James Natale, "Wedges and Corrections for Various Cases of Pronations", *The Master Shoe Rebuilder*, vol. X, No. 2 (Oct. 1950).

Brian A. Rothbart, D.P.M., Ph.D. and Lew Estabrook, D.C., "Excessive Pronation: A Major Biomechanical Determinant in the Development of Chondromalacia and Pelvic Lists", *Journal of Manipulative and Physiological Therapeutics*, vol. 11, No. 5, 373–379 (Oct. 1988).

Brian A. Rothbart, D.P.M., Ph.D., Kevin Hansen, P.T., Paul Liley, D.D.S., and M. Kathleen Yerratt, R.N., "Resolving Chronic Low Back Pain: The Foot Connection", *American Journal of Pain Management*, vol. 5, No. 3, 73 and 84–90 (Jul. 1995).

Brian A. Rothbart, D.P.M., Ph.D., M. Kathleen Yerratt, R.N., "An Innovative Mechanical Approach to Treating Chronic Knee Pain: A Bio–Implosion Model", *American Journal of Pain Management*, vol. 4, No. 3, 123–127 (Jul. 1994).

Primary Examiner—Ted Kavanaugh
(74) Attorney, Agent, or Firm—Christensen O'Connor Johnson Kindness PLLC

(57) ABSTRACT

A forefoot support system 60 for supporting a hyperpronating forefoot 20 both dynamically while the forefoot 20 is in motion and statically is disclosed. The forefoot support system 60 is a bed upon which the forefoot 20 rests which includes an inner edge 62 and an outer edge 64. The forefoot support system 60 is positioned underneath the medial column of forefoot 20. The forefoot support system 60 laterally decreases in thickness from the inner edge 62 to the outer edge 64. The inner edge 62 is positioned along the medial side of the forefoot 20, and the outer edge 64 is positioned longitudinally in a zone substantially between a lateral margin of the hallux 48, the proximal phalanx 46, and the first metatarsal 36 and a medial margin of the phalanges 47 of the second toe and the second metatarsal 38.

18 Claims, 13 Drawing Sheets

U.S. PATENT DOCUMENTS

| | | |
|---|---|---|
| 1,642,764 A | 9/1927 | Brown |
| 1,756,587 A | 4/1930 | Durkee |
| 1,847,973 A | 3/1932 | Morton |
| 1,996,215 A | 4/1935 | Sabiston et al. |
| 2,052,115 A | 8/1936 | Shulman |
| 2,207,833 A | 7/1940 | Stark |
| 2,423,622 A | 7/1947 | Samblanet |
| 2,528,082 A | 10/1950 | Rubico |
| 2,616,190 A | 11/1952 | Darby |
| 2,737,671 A | 3/1956 | Hill |
| 2,933,833 A | 4/1960 | Fiorillo |
| 3,663,978 A | 5/1972 | Meszaros |
| 3,742,627 A | 7/1973 | Schneider |
| 4,360,027 A | 11/1982 | Friedlander et al. |
| 4,642,911 A | 2/1987 | Talarico, II |
| 4,676,801 A | 6/1987 | Lundeen |
| 5,058,585 A | 10/1991 | Kendall et al. |
| 5,327,663 A | 7/1994 | Pryce |
| 5,327,664 A | 7/1994 | Rothbart |
| 5,572,808 A | 11/1996 | Birke |
| 6,092,314 A * | 7/2000 | Rothbart |
| 6,182,380 B1 | 2/2001 | Liley |

* cited by examiner

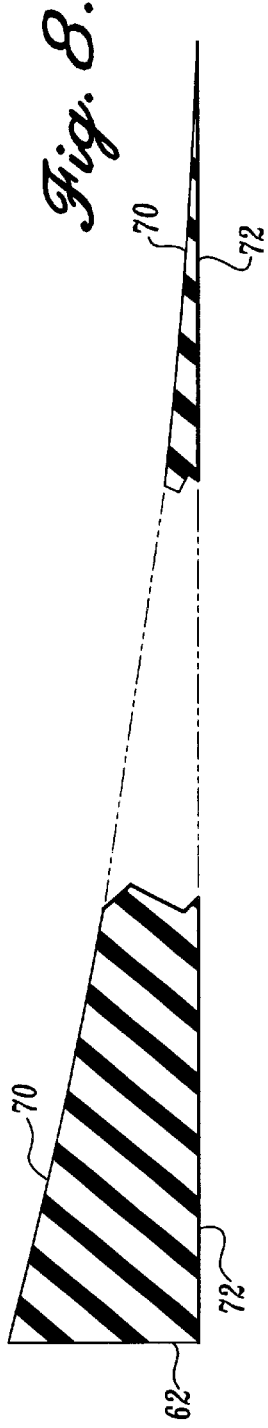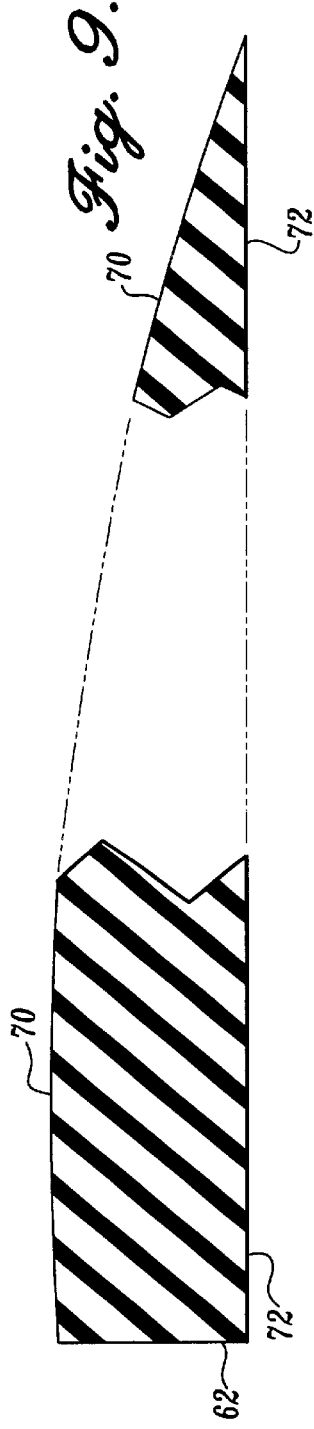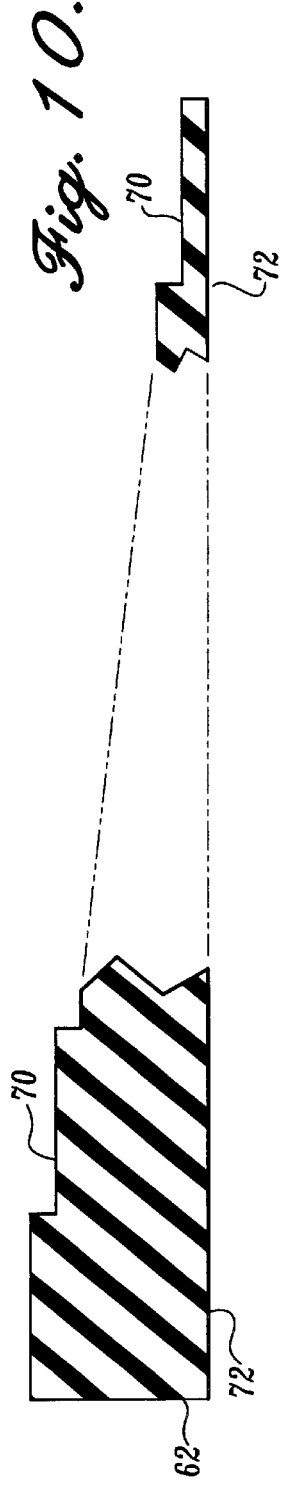

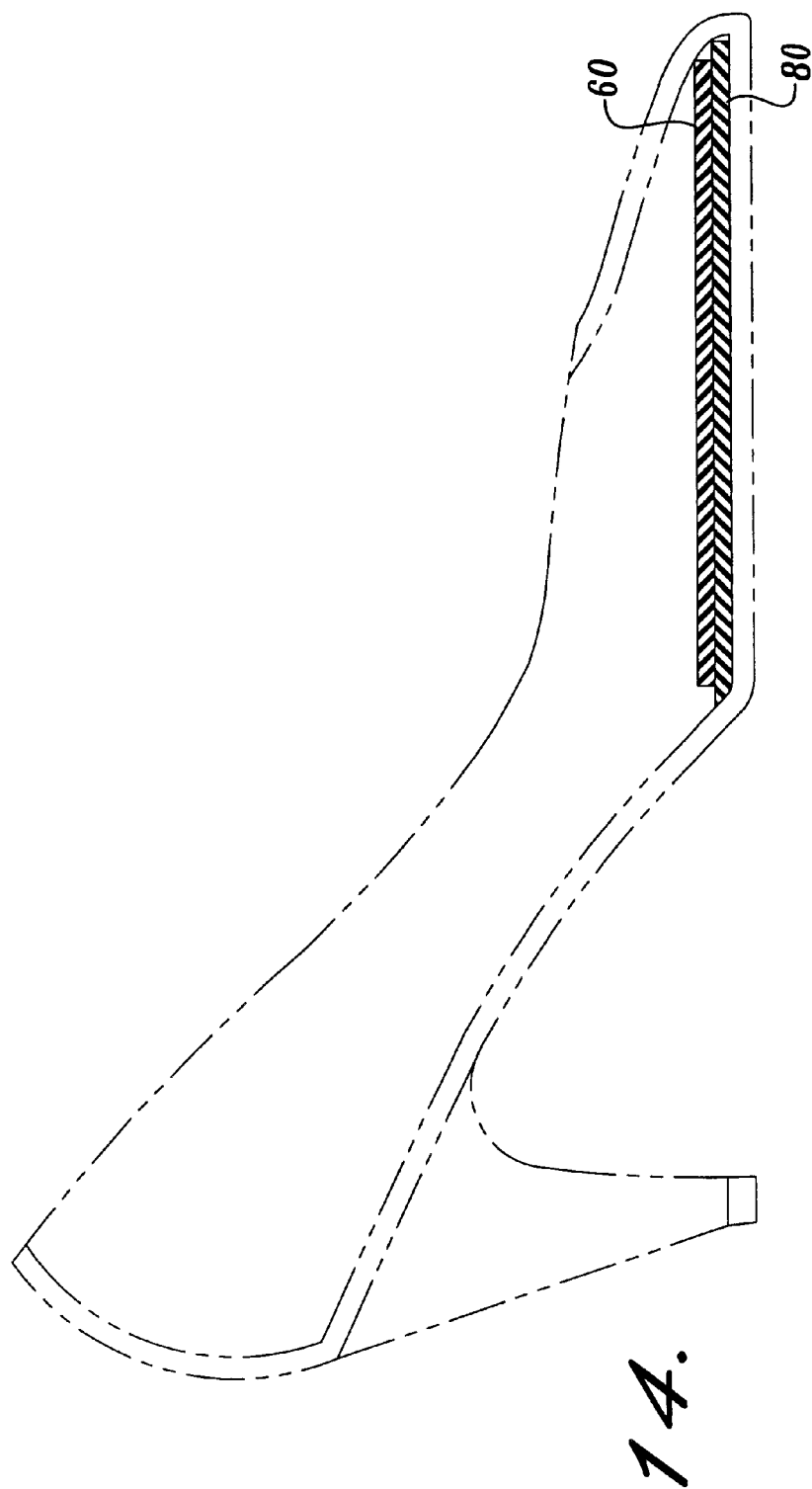

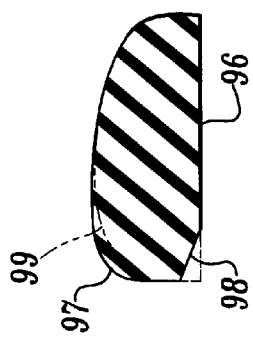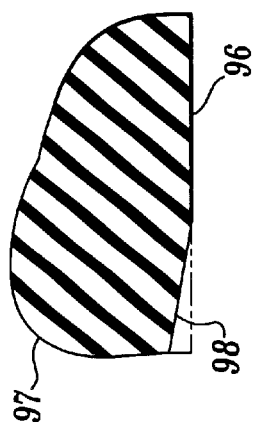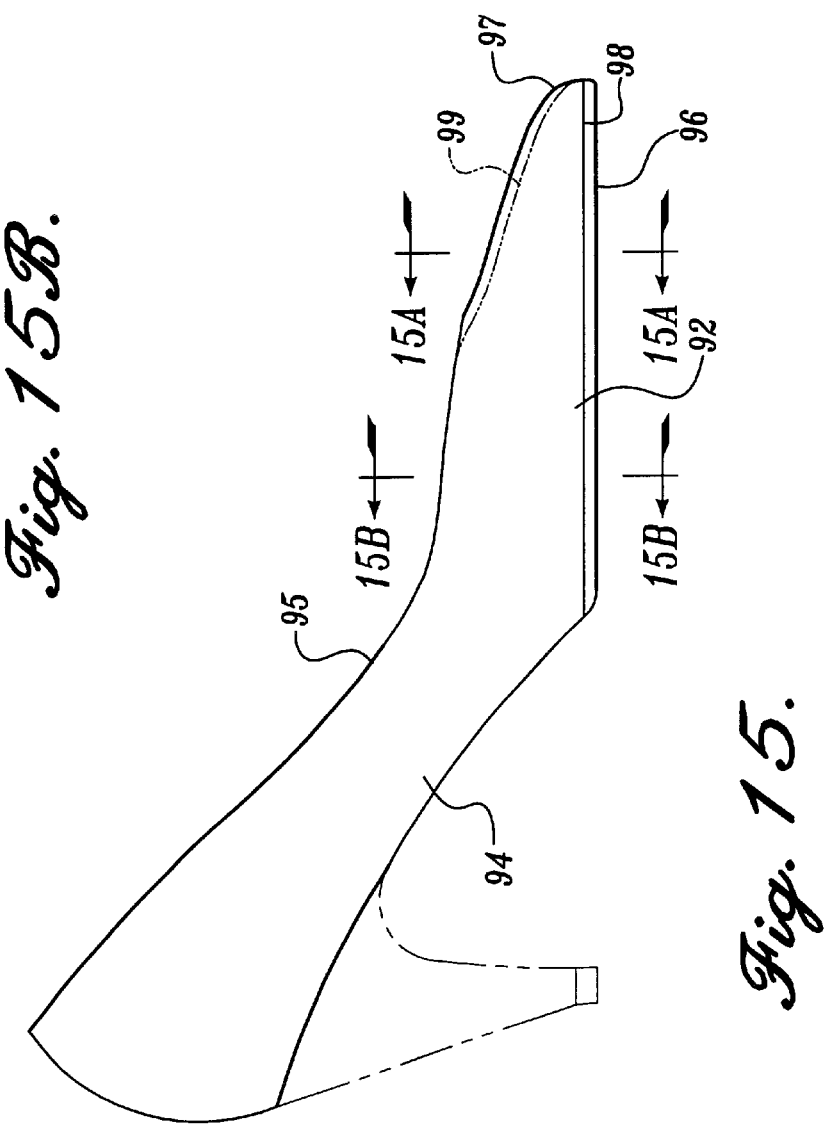

US 6,412,198 B1

FOREFOOT SUPPORT SYSTEM FOR HIGH HEEL SHOES

CROSS-REFERENCE TO RELATED APPLICATIONS

The following application is a continuation-in-part of application Ser. No. 09/413,042, filed Oct. 6, 1999 now U.S. Pat. No. 6,212,723, which is a, continuation of application Ser. No. 09/031,258, filed Feb. 26, 1998, now U.S. Pat. No. 6,092,314, which is continuation-in-part of application Ser. No. 08/733,116, filed on Oct. 16, 1996, now abandoned.

FIELD OF THE INVENTION

This invention relates to forefoot support systems and, more particularly, to forefoot support systems for hyperpronating feet in high heel shoes.

BACKGROUND OF THE INVENTION

Throughout the years people have been continuously searching for better ways to comfort their feet while walking in high heel shoes. One common cause of discomfort associated with walking in high heel shoes is hyperpronation of the feet, especially when wearing high heel shoes with heel heights greater than 2 inches. Hyperpronation is an inward, forward and downward twisting of the forefoot relative to the ground.

To treat and support a hyperpronating forefoot in high heels, foundational stability is provided by maximizing foot-to-ground contact so that the forefoot does not collapse. Traditionally, this is accomplished by orthotic devices. In particular, orthotics for supporting a hyperpronating forefoot are designed to support deficits in a foot's contact with the ground, and in essence function so as to build the ground up to the forefoot.

Presently, some orthotics wedge the forefoot from the medial side to the lateral side of the forefoot. Other orthotics similarly wedge the heel. It is believed that these orthotics, designed to prevent hyperpronation, sufficiently support the static forefoot. However, once the forefoot is it! motion, pronation and discomfort often return. In some instances, this discomfort is partially attributed to the forefoot sliding off the orthotic during gait.

Therefore, there is a need for a forefoot support system that supports a hyperpronating foot both statically and dynamically.

SUMMARY OF THE INVENTION

The present invention is a forefoot support system for supporting a hyperpronating forefoot in high heel shoes both statically and dynamically. The forefoot support system is essentially an elongate bed upon which a portion of the forefoot rests. The forefoot support system includes an inner edge, an outer edge, a front edge and a back edge. The inner edge is positioned along the medial side the forefoot, and the outer edge is positioned longitudinally in a zone substantially between a lateral margin of the hallux, the proximal phalanx, and the first metatarsal head of the forefoot and a medial margin of the phalanges of the second toe and the second metatarsal head. The forefoot support system linearly decreases in thickness from the inner edge to the outer edge. The forefoot support system also extends from the front edge, which is positioned along an anterior end of the hallux, to the back edge, which is positioned just proximal to the first metatarsal head.

In accordance with other aspects of the invention, the forefoot support system decreases in thickness from the inner edge to the outer edge in a concave, convex, or stepped fashion.

In accordance with still other aspects of this invention, the forefoot support system is, preferably, an orthotic.

In accordance with further other aspects of this invention, the forefoot support system also includes a plate having a uniform thickness which is shaped such that it follows the contour of the sole of the forefoot. Further, the plate is positioned either underneath or on top of the elongate bed of the forefoot support system, or, preferably, the plate and elongate bed are integrated to form a single unit. The forefoot support system integrating the plate and elongate bed into a single unit is an insole for inserting in a shoe.

In accordance with further aspects of this invention, the forefoot support system is integrated into a shoe bed of a shoe.

In accordance with yet another aspect of this invention, a last for making a shoe is provided which incorporates the forefoot system of the present invention.

As will be readily appreciated from the foregoing description, the invention provides a forefoot support system that supports the medial column of the forefoot from the anterior end of the hallux to a position just proximal to the first metatarsal head, and thus supports a forefoot having Rothbart's Foot Structure and prevents hyperpronation. Because the forefoot support system extends to the hallux, and because in high heel shoes the body's weight is predominately over the ball (metatarsal heads and phalanges) of the foot, the forefoot is supported in its anatomical position not only while standing but also during toe-off while in motion. Therefore, the forefoot support system of the present invention more fully supports a hyperpronating forefoot and decreases discomfort associated therewith.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 8 is a partial cross-sectional view of an alternative embodiment of the forefoot support system illustrating a concave slope along the upper surface of the forefoot support system;

FIG. 9 is a partial cross-sectional view of yet another alternative embodiment of the forefoot support system illustrating a convex slope along the upper surface of the forefoot support system;

FIG. 10 is a partial cross-sectional view of yet still another alternative embodiment of the forefoot support system illustrating a stepped slope along the upper surface of the forefoot support system;

FIG. 14 is a perspective view of an alternative embodiment of the forefoot support system depicting the forefoot support system embedded in a shoe bed of a shoe;

FIG. 15 is a side view of a last for making shoes incorporating the forefoot support system according to the present invention;

FIG. 15A is a cross-sectional view of the last of the present invention taken along line 15A—15A of FIG. 15;

FIG. 15B is a cross-sectional view of the last of the present invention taken along line 15B—15B of FIG. 15;

DETAILED DESCRIPTION OF THE PREFERRED EMBODIMENT

The present invention is directed to a forefoot support system that supports a hyperpronating forefoot, specifically in high heel shoes, both statically and dynamically. Although some have theorized about the cause of hyperpronation, it has never been sufficiently understood. In order to adequately prevent hyperpronation and the discomfort associated therewith, however, such an understanding is necessary. In this regard, in order to better understand the present invention, a brief review of the embryological development of the lower limb bud and foot is necessary. This discussion will elucidate the spatial derangement of the foot and lead to the necessity for using the forefoot support system of the present invention.

Figure 1:
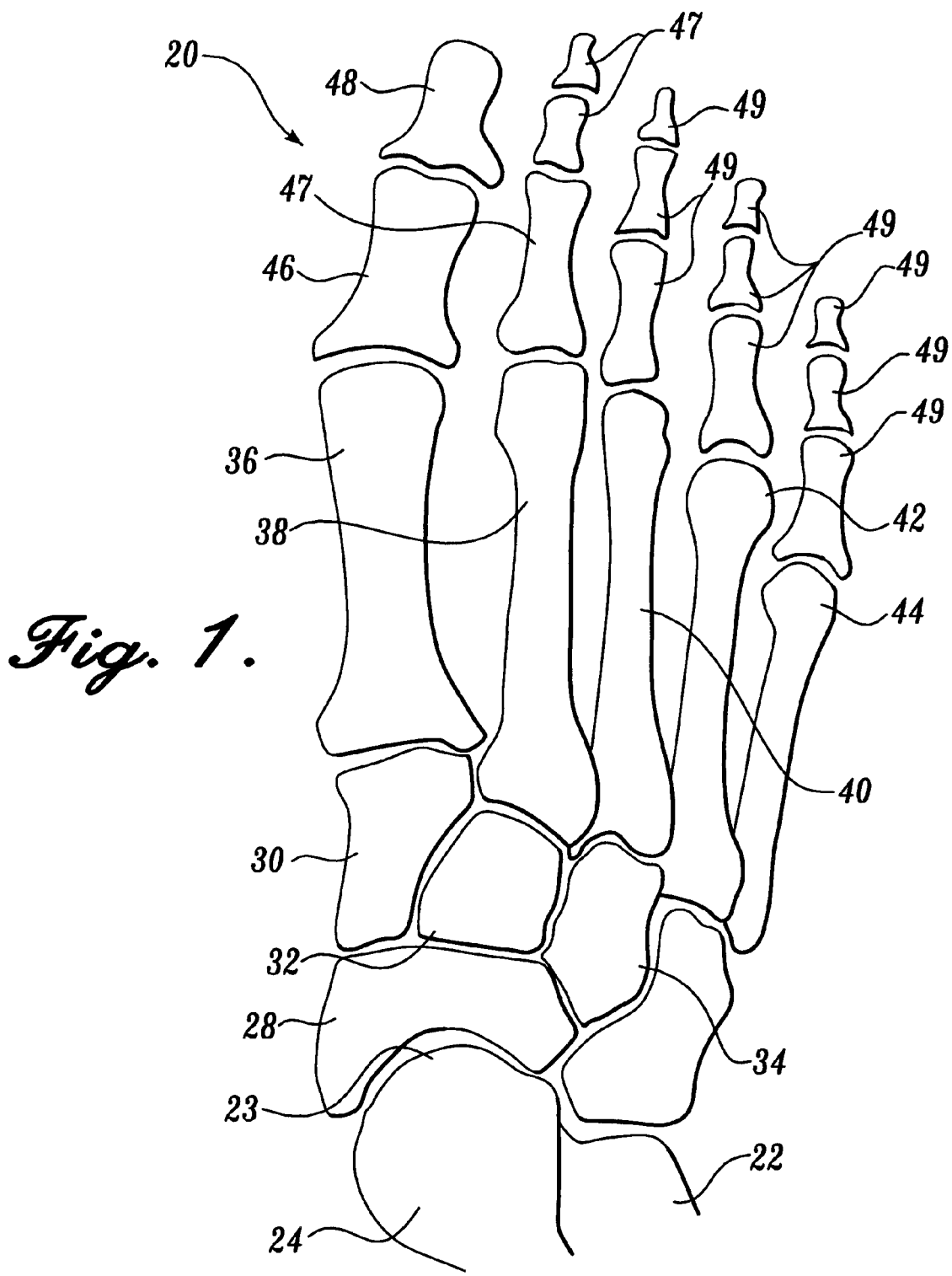
FIG. 1 is a top view of a foot depicting a plurality of bones in the foot.

For reference, FIG. 1 illustrates a plurality of bones in an adult foot 10. The adult foot 10 includes a forefoot 20 and rearfoot 14. The bones shown in rearfoot 14 include a calcaneus 22, a talus 24 having a talar head 23 and a talar neck, a navicular 28, a medial cuneiform 30, an intermediate cuneiform 32, and a lateral cuneiform 34. The bones shown in forefoot 20 include a first metatarsal 36, a second metatarsal 38, a third metatarsal 40, a fourth metatarsal 42, a fifth metatarsal 44, a proximal phalanx 46, a hallux 48, a plurality of phalanges 47 of the second toe, and a plurality of phalanges 49 of the third, fourth and fifth toes. The hallux 48 and the proximal phalanx 46 are also referred to as the phalanges of the first toe. The first metatarsal includes a metatarsal head 37 disposed distally away from the medial cuneiform and adjacent to the posterior end of the proximal phalanx.

Figure 2:
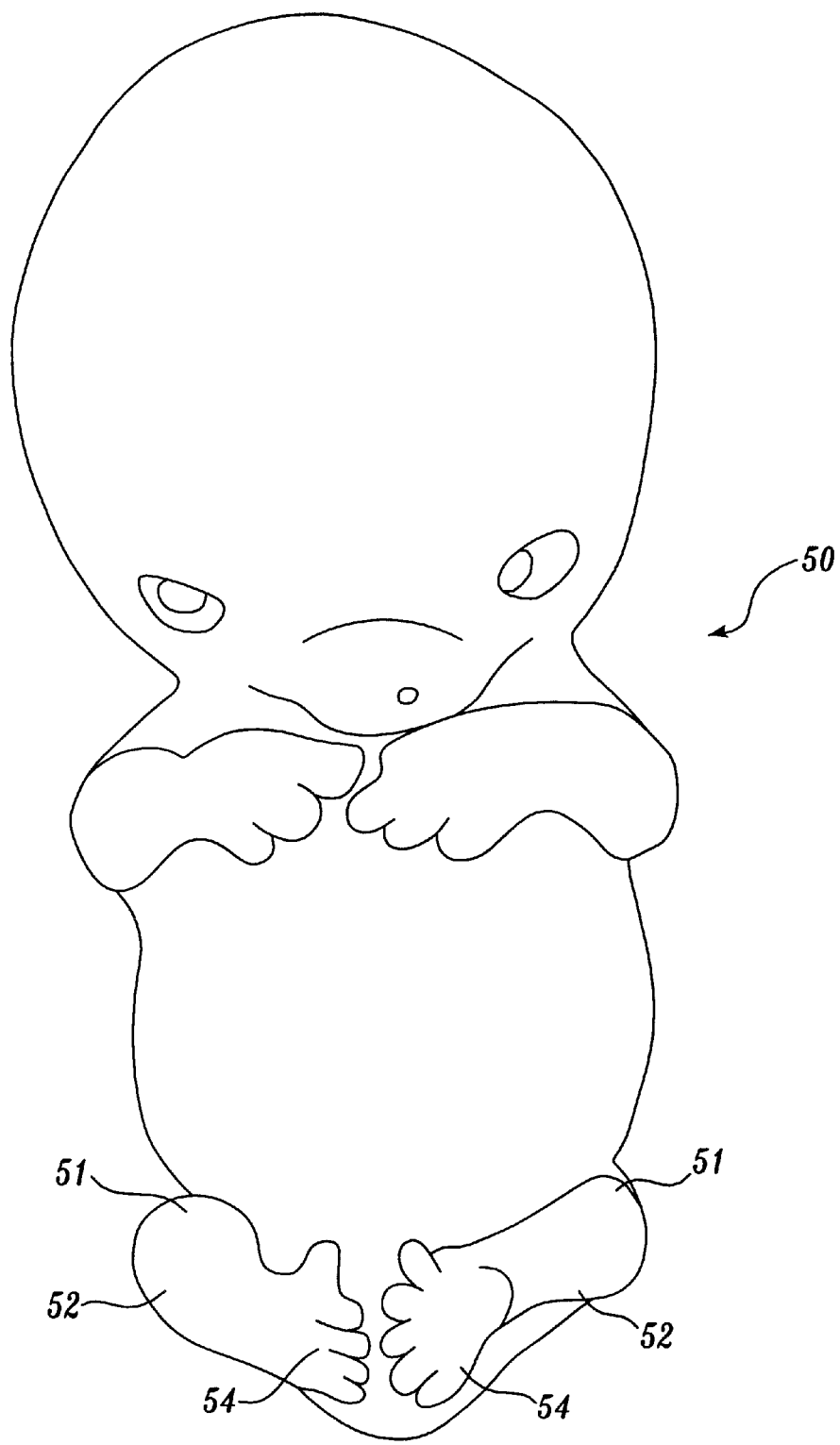
FIG. 2 is a perspective view of an embryo at 8 weeks post fertilization.

FIG. 2 illustrates a fetus 50 at the end of the embryonic period at 8 weeks post fertilization (pt). The fetus 50 has lower limbs, each corresponding to a thigh 51, a lower leg 52 and a foot 54. The lower limbs lie in a sagittal plane, as shown in FIG. 2. The lower limbs are externally rotated relative to the midline of the body such that the posterior side of the thighs and lower legs and the soles of the feet are facing one another. Furthermore, the foot 54 lies in an extreme plantarflexed position relative to the lower leg 52.

During fetal development, important axial rotational changes occur that alter the foot to leg relationship. Generally, there is a progressive internal rotation of the thigh-lower leg-foot segments which occurs in a sequential pattern. Initially, the thigh-lower leg segment internally rotates, the right thigh-lower leg segment rotating counter-clockwise and the left rotating clockwise. This positions the foot 54 so that it is plantarflexed and externally rotated relative to the lower leg 52.

Then, between 8 and 12 weeks pf, the foot undergoes dramatic reorientation. By week 9 pf, the ankle joint is forming, taking the foot out of its extreme plantarflexed position. The feet are still on the sagittal planes, soles facing each other. The resulting foot to lower leg relationship is termed supinatus. At week 10 pf, the foot begins to unwind, starting proximally at the heel and progressing distally through the inner arch and rest of the forefoot. Initially, the posterior surface of the calcaneus begins to untwist, the right heel bone in a counterclockwise direction and the left heel bone in a clockwise direction. Thus, the rearfoot is no longer in supinatus. For a brief period of time, the foot appears tortuously twisted, heel to ball. Shortly thereafter, the head and neck of the talus, also referred to as the talar head and neck, begin to untwist. This untwisting of the talus reduces the supinatus within the ball of the foot as the talar head carries the navicular, internal cuneiform, first metatarsal, proximal phalanx and hallux out of supinatus into their proper positions. By week 36 pf, the untwisting process is almost completed and the fetal foot resembles that of the adult foot. Furthermore, the foot supinatus is no longer apparent.

Figure 3:
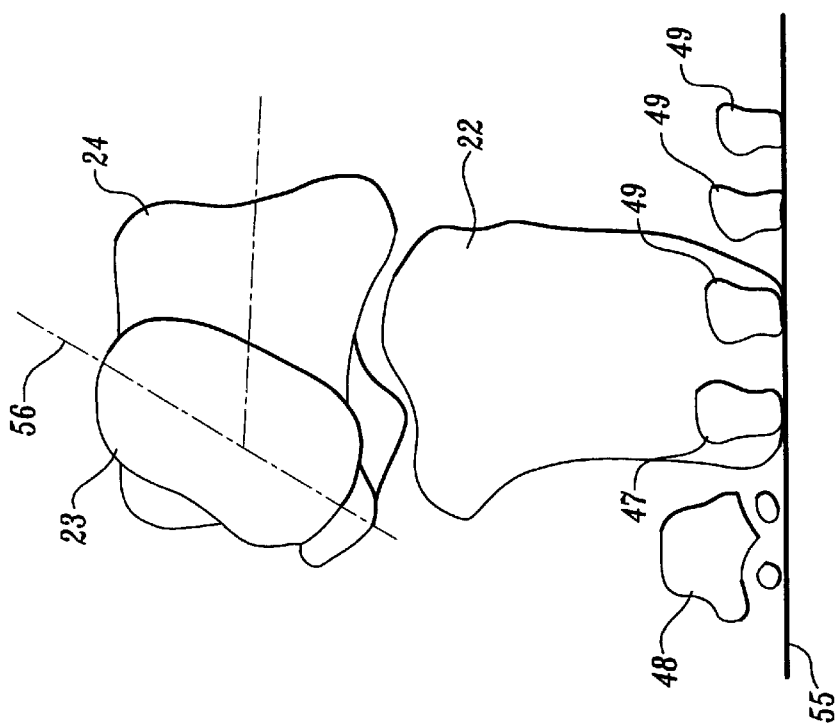
FIG. 3 is a front view of a mechanically stable adult foot.

FIG. 3 illustrates a front skeletal view of an adult foot which has fully completed the untwisting process. As shown in FIG. 3, the hallux 48, the phalanges 47 of the second toe, and the phalanges 49 of the third, fourth and fifth toes are in full contact with a ground level 55. Furthermore, the head 23 of the talus 24 is depicted in its completely unwound position. For reference, an axis 56 through the completely unwound talar head 23 forms approximately a 50-degree angle relative to the ground level 55.

However, if the talar head 23 does not untwist, the entire inside of the foot, excluding the heel, is affected. In 1906, R. S. Sewell, in *A study of the asragulus,* Part IV, J Anat Physiol 40:152, reported up to a 20 degree twist in the talar head, a condition he refers to as talar supinatus. The inventor has discovered the effect talar supinatus has on the first metatarsal 36, proximal phalanx 46 and hallux 48, hereinafter, the medial column, relative to the other bones of the forefoot. In this regard, the inventor has observed up to 35 mm of dorsal displacement of the medial column. The twist and dorsal displacement of the medial column is hereinafter referred to as Rothbart's Foot Structure.

Figure 4:
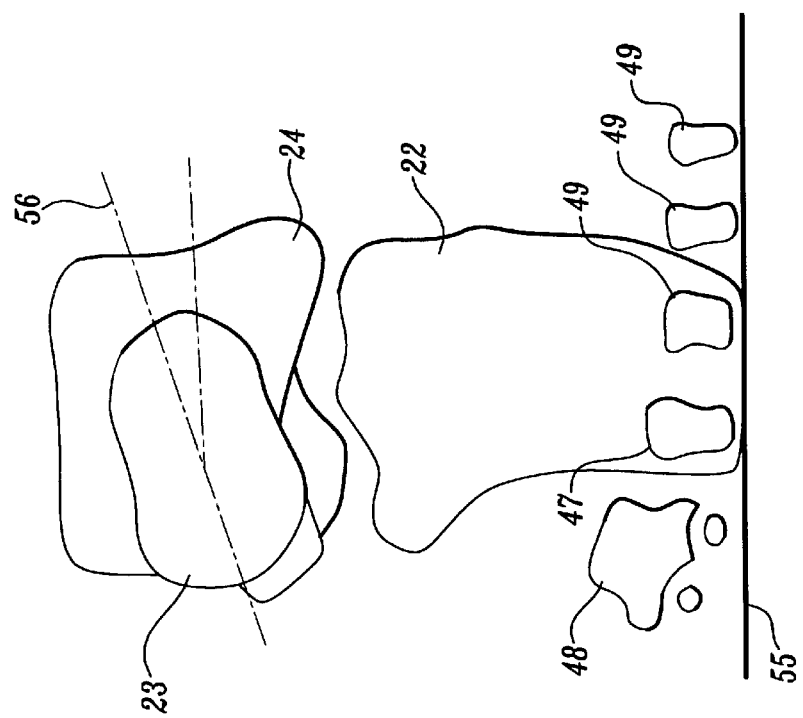
FIG. 4 is a front view of an adult foot having Rothbart's Foot Structure, depicting a twisted talar head and an elevated medial column of the foot.

FIG. 4 illustrates a front view of an adult foot which has not completed the untwisting process, thus having Rothbart's Foot Structure. As shown in FIG. 4, the phalanges 47 of the second toe and the phalanges 49 of the third, fourth and fifth toes are in full contact with ground level 55. However, the hallux 48 is shown elevated and twisted relative to the ground level 55 since the inside column of the foot has not completely unwound. Furthermore, the axis 56 running through the head 23 of the talus 24 now forms approximately a 30-degree angle with respect to the ground level 55. This change in rotation of axis 56 represents the twist remaining in the talar head 23, as it too did not completely unwind. For one skilled in the art, it will be appreciated that the degree of twist of the medial column of a forefoot having Rothbart's Foot Structure can vary depending on an individual's degree of deformity.

The timing of the lower limb bud's untwisting process explains the pathoembryological cause of both Rothbart's Foot Structure and clubfoot deformity. As indicated by G. L. Streeter and indicated above, the leg and foot untwist proximal to distal. See, Streeter, G L. "Developmental horizons in human embryos." *Contributions to Embryology*, Vols. 21, 32, 34. Washington D.C. Carnegie Institution of Washington, 1945, 1948, 1951. It does so in a temporally contiguous pattern, as follows: femur, tibia, calcaneum, and finally talus. If the untwisting process prematurely ends at the level of the calcaneum, this condition is called clubfoot deformity. If the untwisting process prematurely ends at the level of the talus, this condition is Rothbart's Foot Structure. Skeletal studies by Sewell, Olivier and Straus have demonstrated that heel bone supinatus is a component of the clubfoot deformity. See Olivier G. *Formation du Squelette des membres*. Pages 145–189. Paris, vigot Freres, 1962; and Straus, W L Jr. "Growth of the human foot and its evolutionary significance." *Contrib Embryol* 19:95, 1927. The inventor notes that in a differential diagnosis of the adult foot, when clubfoot deformity is ruled out, heel bone supinatus is concurrently ruled out. That is, heal bone supinatus cannot exist by itself. Recent clinical studies by the inventor and other clinical studies have allowed the inventor to first conclude that Rothbart's Foot Structure can exist alone or as part of a clubfoot deformity.

Additionally, Rothbart's Foot Structure has a dramatic effect on the relative length pattern between metatarsals 1 and 2. The retained twist within the talar bone elevates, twists, and proximally displaces the first metatarsal bone (similar to bowleggedness shortening the tibia). Radiographically, the first metatarsal appears 10–20 mm shorter than the second metatarsal. D J Morton was the first to clinically identify and publish on a short first metatarsal. See Morton, D J. *The Human Foot. Its Evolution, Physiology and Functional Disorders*. Columbia University Press, New York, 1935. However, Morton failed to recognize Rothbart's Foot Structure, i.e., the elevated and twisted displacement of the medial column of the forefoot. More recently, Janet Travell has linked Rothbart's Foot Structure to the "activation and perpetuation of trigger points." It is these trigger points that lead to chronic musculoskeletal symptoms, including knee, hip and back pain.

The accumulative data from the above-mentioned skeletal and clinical studies indicates that the primary cause of hyperpronation is Rothbart's Foot Structure. Furthermore, it is believed that the diagnosis of Rothbart's Foot Structure, in most cases, precludes heel bone supinatus. Thus, in high heel shoes, wedging the heel bone or supporting the arch to treat Rothbart's Foot Structure is mechanically inefficient because these structures only marginally participate in weight bearing. Review of the biomechanical literature reveals that this is a common practice in treating hyperpronation. Although wedging the heel bone does decrease the observed secondary hyperpronation generated at heel contact, it does not address the primary hyperpronation generated at toe-off during gait. Furthermore, since heel bone supinatus is rarely seen in the adult forefoot, wedging the heel bone is avoided.

In differentiating Rothbart's Foot Structure from other structural anomalies, it is important to remember that the retained twist in the talus effects the medial column of the forefoot. It does not impact the heel bone, lateral column of the foot or metatarsals 2–5. As a result, it is believed that the most effective way to attenuate hyperpronation is to support the medial column of the forefoot in its anatomical neutral position. Thus, the present invention is directed to a forefoot support system that effectively builds the ground up to the medial column of a forefoot exhibiting Rothbart's Foot Structure, thereby supporting the forefoot in its anatomical position so that the forefoot does not inwardly collapse or hyperpronate.

Figure 5:
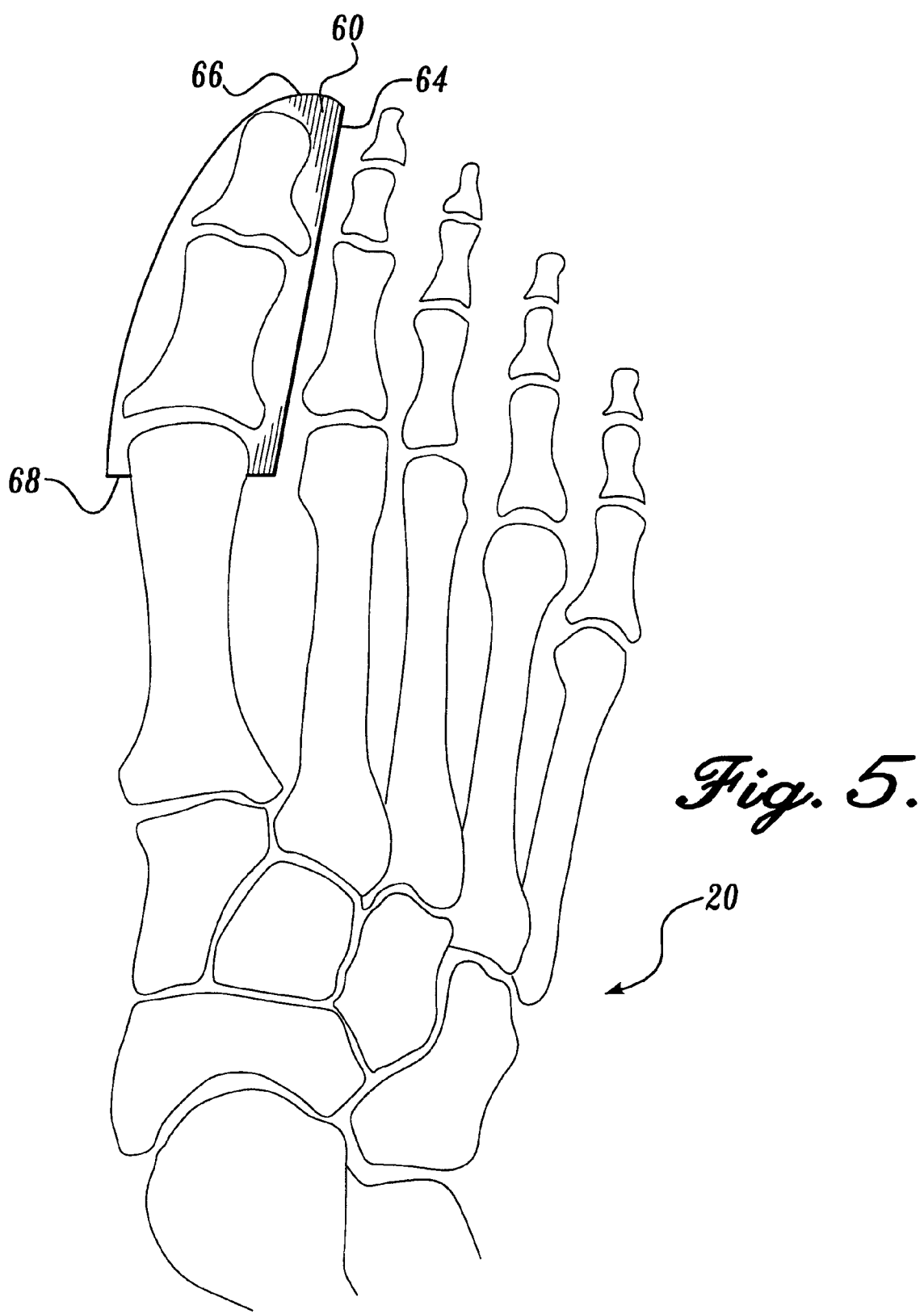
FIG. 5 is a top view of a forefoot depicting a forefoot support system according to the present invention underlying a portion of the forefoot.
Figure 6:
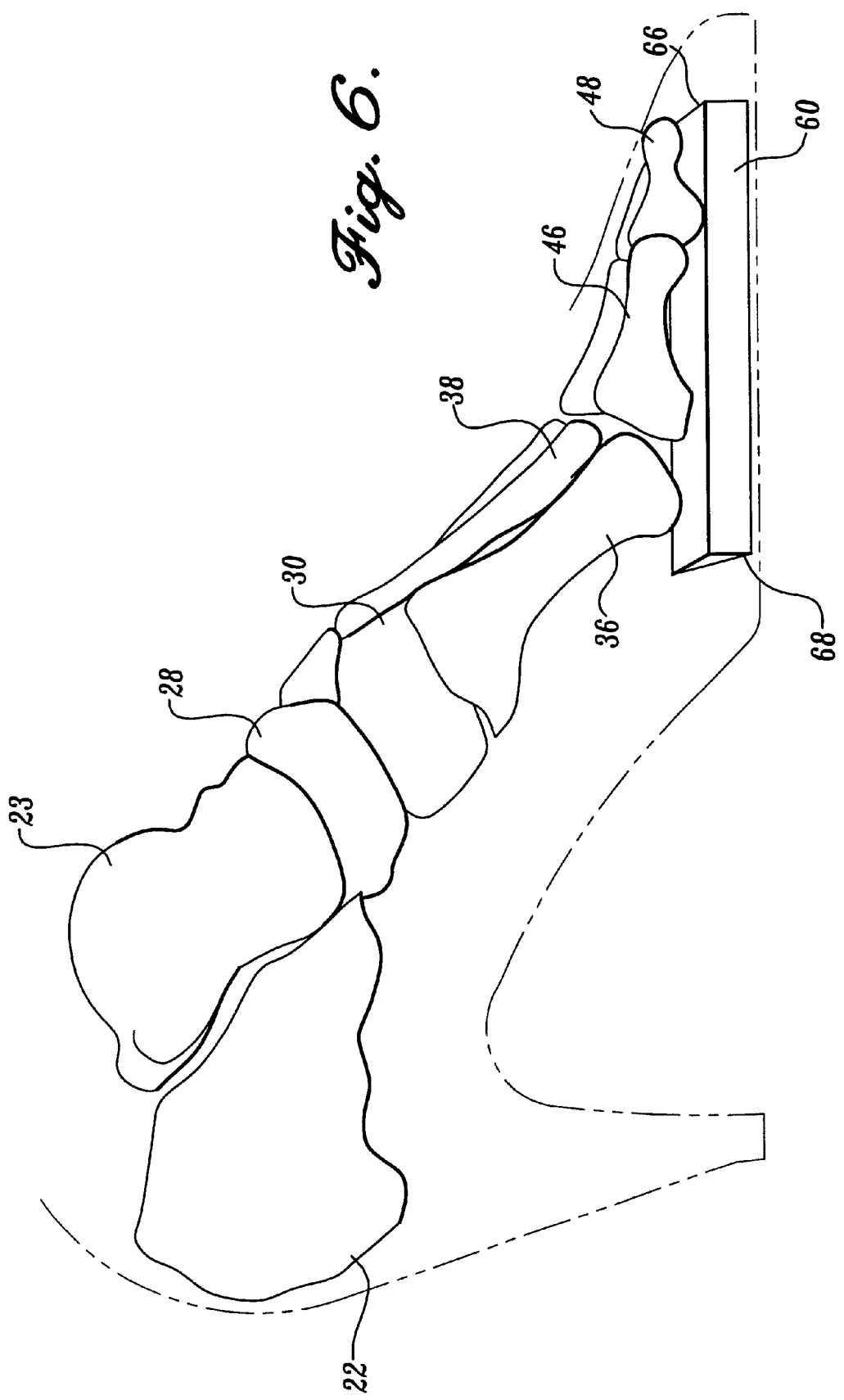
FIG. 6 is a side view of the forefoot support system of the present invention positioned underneath the medial column of a forefoot.

FIG. 5 illustrates a top view of a forefoot support system 60 underlying a portion of forefoot 20. Forefoot support system 60 is an elongate bed upon which a portion of the forefoot 20 rests which includes an inner edge 62, an outer edge 64, a front edge 66, and a back edge 68. The forefoot support system 60 is positioned underneath the medial column of forefoot 20 and extends from the hallux 48 to just proximal to the first metatarsal head 37. From a side view of the support system 60 underlying the medial column of the forefoot 20, as shown in FIG. 6, the forefoot support system 60 extends from an anterior end of the hallux 48 to just proximal to the first metatarsal head 37. Preferably, the front edge 66 is coincident with the anterior end of the hallux 48, and the back edge 68, although lying just proximal to the first metatarsal head 37, is coincident with the surgical neck of the first metatarsal, defined by the first metatarsal head 37. However, it will be appreciated by one skilled in the art that the front edge 66 may also lie in a position anterior to the hallux 48, while the back edge 68, although lying just proximal of the first metatarsal head 37, may lie in a position midshaft of the first metatarsal.

As shown in FIG. 5, the inner edge 62 is positioned along and follows the contour of the medial side of the forefoot 20. The outer edge 64 lies longitudinally in a zone substantially between a lateral margin of the hallux 48, the proximal phalanx 46 and the first metatarsal head 37 and a medial margin of the phalanges 47 of the second toe and the second metatarsal head of the second metatarsal 38, and does not significantly elevate the phalanges 47 of the second toe, or the second metatarsal 38. Elevating the phalanges of the second toe and the second metatarsal by 3 millimeters or greater is considered significant. Preferably, the outer edge 64 lies along the lateral margin of the hallux 48, the proximal phalanx 46 and the first metatarsal head 37.

Figure 7:
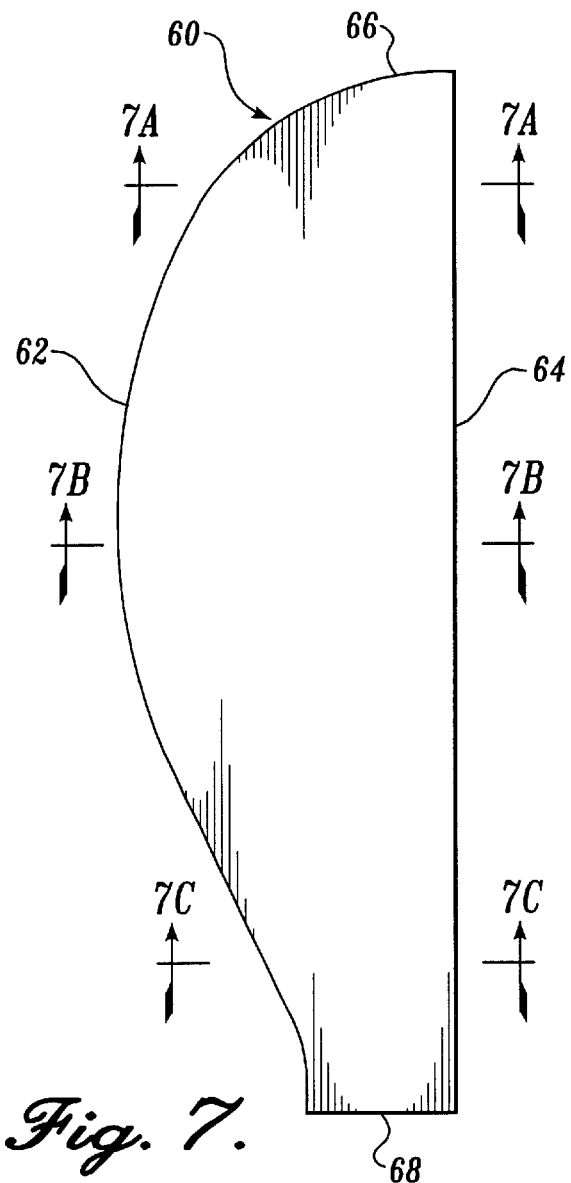
FIG. 7 is a top view of the forefoot support system of the present invention showing several cross-sectional portions.
Figure 7A:
FIG. 7A is a cross-sectional view of the forefoot support system of the present invention taken along line 7A—7A of FIG. 7.
Figure 7B:
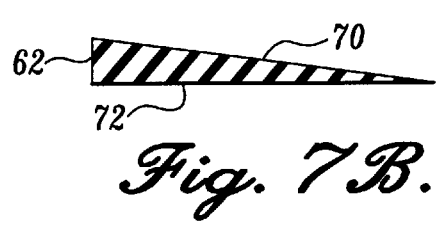
FIG. 7B is a cross-sectional view of the forefoot support system of the present invention taken along line 7B—7B of FIG. 7.
Figure 7C:
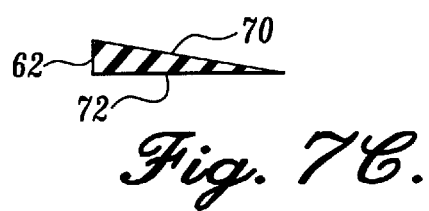
FIG. 7C is a cross-sectional view of the forefoot support system of the present invention taken along line 7C—7C of FIG. 7.

FIG. 7 is a top view of the forefoot support system 60, and FIGS. 7A, 7B, and 7C are cross-sectional views of the forefoot support system 60 taken respectively along lines 7A—7A, 7B—7B, and 7C—7C of FIG. 7. As shown in FIGS. 7A, 7B, and 7C, the forefoot support system 60 also includes an upper surface 70 on which the forefoot 20 rests and a lower surface 72. The forefoot support system 60 further includes a vertical component such that when the forefoot support system 60 is positioned underneath the forefoot, the medial column of the forefoot is supported in an elevated position relative to the remainder of the forefoot.

More particularly, the forefoot support system 60 decreases in thickness from the inner edge 62 to the outer edge 64 such that the upper surface 70 slopes downwardly from the inner edge 62 to meet the lower surface 72 at the outer edge 64. Preferably, the upper surface 70 slopes downward linearly, such that the forefoot support system 60 is wedge-shaped. However, it will be appreciated that the upper surface 70 can also slope downward in a concave, convex or stepped fashion. See FIGS. 8–10, respectively.

Furthermore, although the upper surface 70 preferably slopes downward to meet the lower surface 72 at the outer edge 64 such that the outer edge 64 has no vertical component, it will be appreciated that the upper surface 70 can also slope downward to the outer edge 64 without meeting the lower surface 72 such that the outer edge 64 has some thickness.

Figure 11:
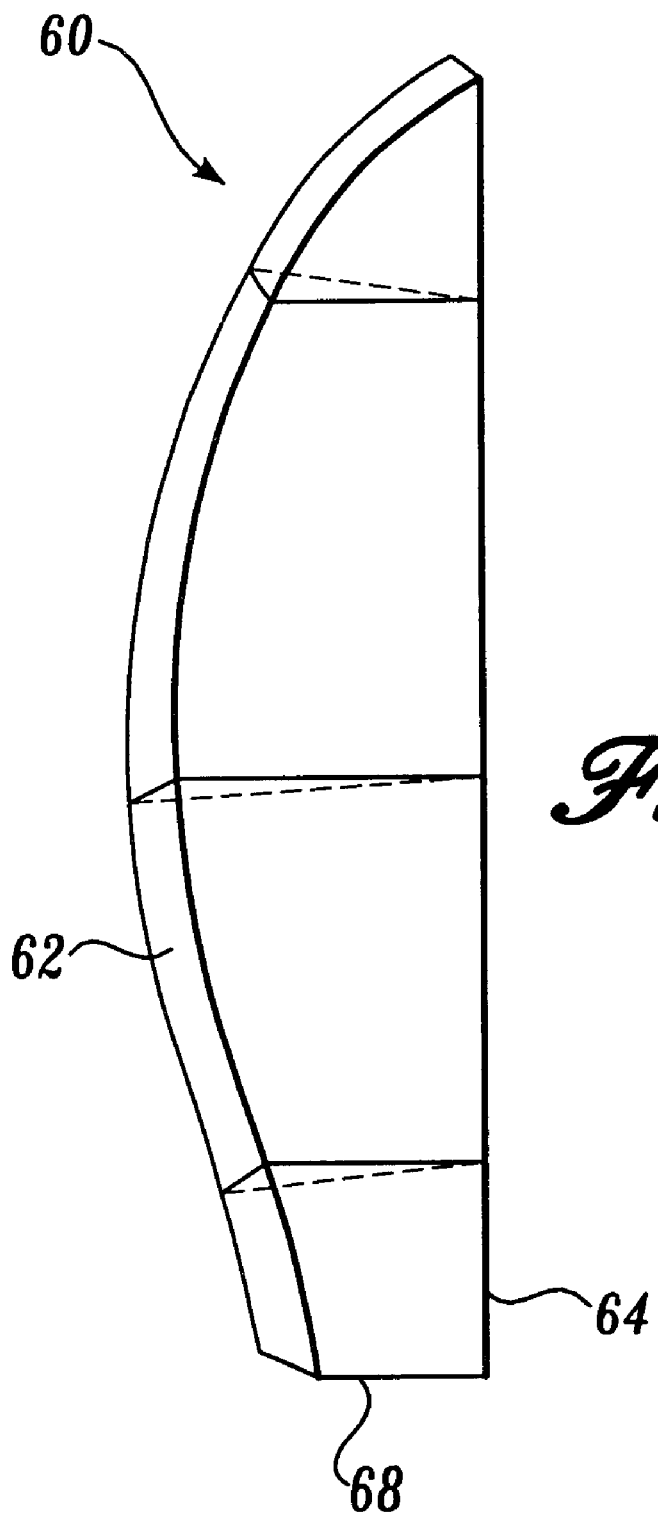
FIG. 11 is a perspective view of the forefoot support system of the present invention.

As shown in a perspective view of the forefoot support system 60 in FIG. 11, the thickness or height of the inner edge 62 of the forefoot support system 60 is uniform. However, it will be appreciated that, besides sloping downwardly from the inner edge 62 to the outer edge 64 of the forefoot support system 60, the upper surface 70 can also slope downwardly or taper as it extends forward toward the front edge 66. Furthermore, the upper surface 70 can, alternatively or additionally, slope downwardly or taper as it extends back toward the back edge 68.

As shown in both FIGS. 7 and 11, the forefoot support system 60 varies in width, with the widest portion of the forefoot support system 60 underlying the proximal phalanx and the head of the first metatarsal. As the forefoot support system extends from its position under the proximal phalanx to the front edge 66 and to the back edge 68 of the forefoot support system 60, the width narrows due to the contoured shape of the medial side of the forefoot. As shown in FIGS. 7A, 7B, and 7C since the thickness or height of the forefoot support system 60 is uniform along the inner edge 62, the slope of the upper surface 70 varies depending upon the width of the lower surface 72 of the particular cross-section. In particular, in the wedge-shaped cross-section taken from the widest portion of the forefoot support system, shown in FIG. 7B, the slope of the upper surface 70 decreases more gradually than the slope in the cross-section taken from the narrowest portion of the forefoot support system as shown in FIG. 7C.

Figure 12:
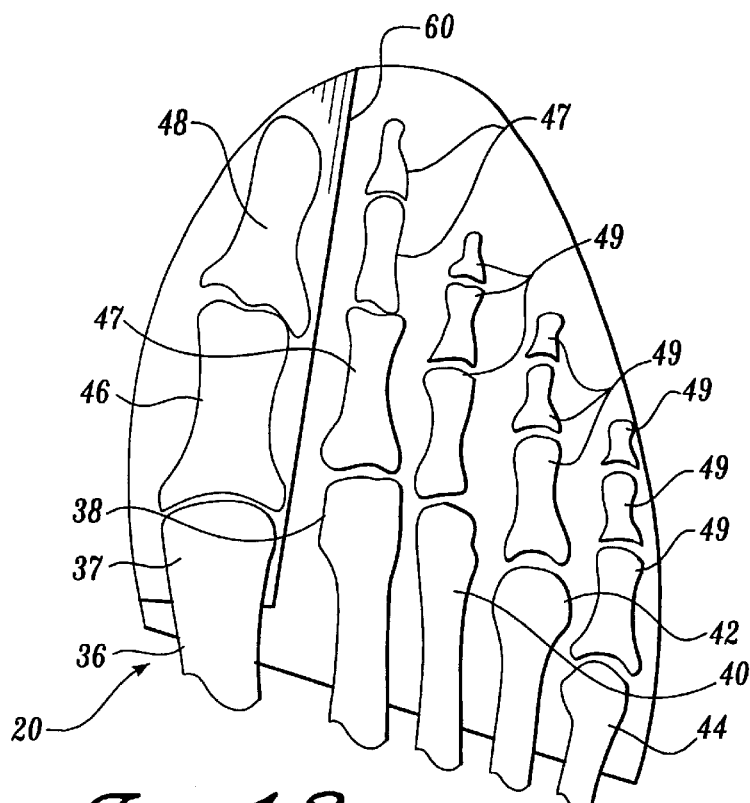
FIG. 12 is a top view of a forefoot support system of the present invention underlying a portion of the forefoot in position on top of a plate.
Figure 13:
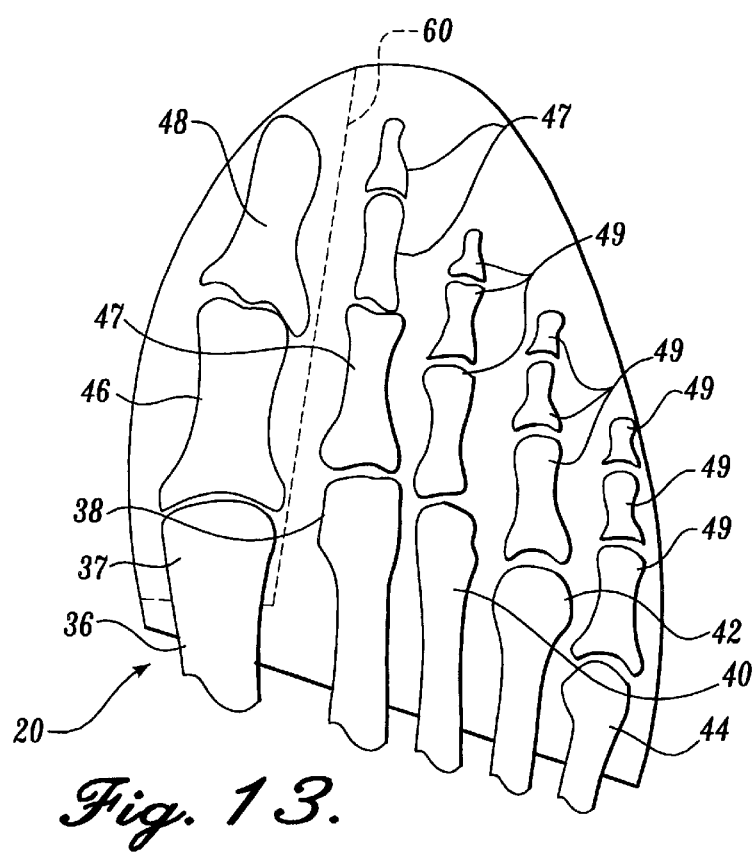
FIG. 13 is a top view of a forefoot support system of the present invention underlying a portion of the forefoot and positioned underneath a plate.

FIG. 12 illustrates a top view of the forefoot support system 60 positioned underneath the hallux 48, the proximal phalanx 46, and the first metatarsal head 37 of the first metatarsal 36 and further positioned on top of a plate 80. Plate 80 is shaped such that it follows the outer contour of the forefoot 20. Preferably, the forefoot support system 60 is an orthotic for wearing in a high heel shoe, where plate 80 represents an interior bed of the high heel shoe. However, it will be appreciated that the forefoot support system 60 and the plate 80 can be an integrated unit such that together they form an insole for inserting within the high heel shoe. If the support system is incorporated into an insole, the plate 80 has no vertical rise in any area of the plate. Rather, plate 80 is flat and has a uniform thickness. Furthermore, plate 80 can be positioned either on top of, as show in FIG. 12, or underneath, as shown in FIG. 13, the forefoot support system 60. Regardless, the plate's main function, in this instance, is to maintain the proper fit between the forefoot and the forefoot support system 60.

In another alternative embodiment, the forefoot support system 60 is built into a high heel shoe having a shoe bed, such that the shoe bed incorporates the forefoot support system 60 therein. FIG. 14 is a side cross-sectional view of a high heel shoe in which the forefoot support system 60 is incorporated into the shoe bed thereof. In this embodiment, the plate 80 and forefoot support system 60, as an integrated unit, represent the shoe bed of the high heel shoe incorporating the forefoot support system 60. Since shoes are built using a last around which the shoe is formed, a shoe incorporating the forefoot support system 60 is preferably made with a last specially designed for creating the forefoot support system 60 in the shoe bed.

FIG. 15 illustrates a medial side view of a last 90 for making shoes which incorporate the forefoot support system 60. Last 90 is essentially the shape of a foot and includes a forefoot portion 92, a rearfoot portion 94, a top surface 95, a bottom surface 96, and an upper forefoot surface 97. The last 90 also contains a cavity that runs longitudinally and laterally underneath the medial column of the last 90 and that has the same shape as the forefoot support system 60, as described above.

Figure 16:
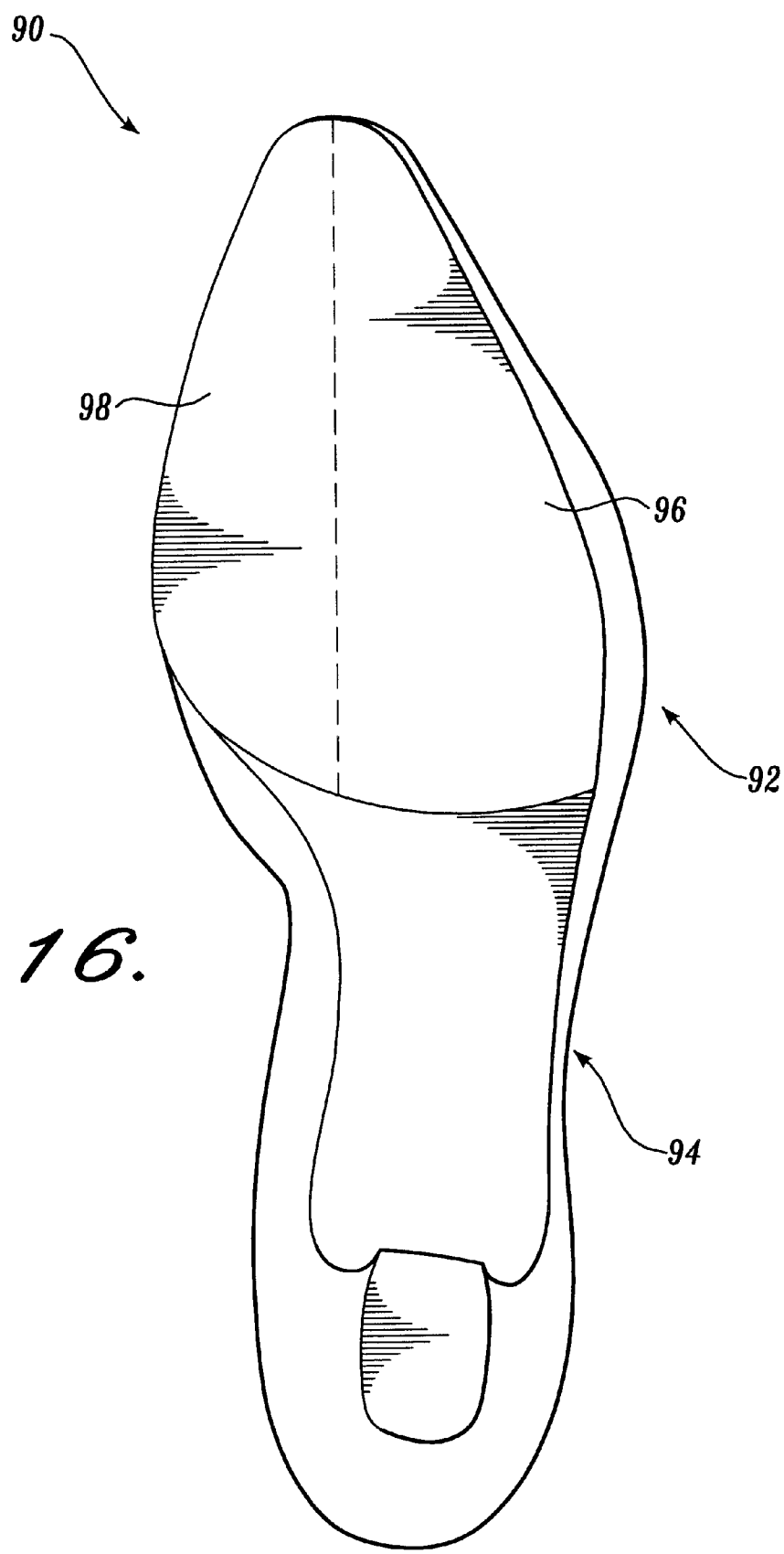
FIG. 16 is a plain view of a bottom surface of the last of the present invention.

As shown in FIG. 16, in a bottom view of last 90, the bottom surface 96 has an inner edge portion 98 which corresponds to the location of the cavity. The inner edge portion 98 extends from the front of the forefoot portion 92 to a position just proximal to the back of the forefoot portion 92, but does not extend into the rearfoot portion 94 which corresponds to the mid-metaphysis of the metatarsal bones. FIG. 16 illustrates the inner edge portion 98 extending from the front to the back of the forefoot portion 92. Furthermore, the inner edge portion 98 of the bottom surface 96 is elevated with respect to the remainder of the bottom surface, so as to adjust for the cavity corresponding to the forefoot support system 60. More particularly, the bottom surface 96 laterally slants downward across the inner edge portion 98 beginning at the medial side of the last:

As shown in FIG. 15 in a cross-sectional view taken along line 15A—15A of FIG. 15, the inner edge portion 98 of the bottom surface 96 of the last 90 slopes downwardly from the medial side of the last to a longitudinal position where it meets the remainder of the bottom surface 96. This longitudinal position lies in a zone substantially between the lateral margin of the phalanges of the first toe and of the first metatarsal head and the medial margin of the phalanges of the second toe and the second metatarsal head, as described above. Also, as similarly described above in reference to the forefoot support system 60, the inner edge portion 98 of the bottom surface 96 can be downwardly sloped in a linear, convex, concave, or other similar manner.

In a last for making a shoe that does not incorporate the forefoot support system 60, the bottom surface of the last in any cross section taken from the medial to the lateral side of the last, other than in the inner arch section, is substantially flat. However, in a last for making a shoe incorporating the forefoot support system of the present invention, any cross sections taken from the medial to the lateral side of the forefoot portion 92 of the last 90 illustrate a downwardly sloped inner edge portion 98 of the bottom surface 96. Thus, when the shoe is formed around the last, the shoe contains a forefoot support system 60 as described above for supporting the medial column of the forefoot, including the hallux, the proximal phalanx, and the first metatarsal head.

Additionally, in the last of the present invention as shown in FIG. 15A, the upper forefoot surface 97 along the medial column of the last 90 extends outwardly from an upper forefoot surface 99, representing the upper forefoot surface of a last which does not incorporate the forefoot support system 60. The upper forefoot surface 97 along the medial column of the last extends outwardly in order to make more space for the inner column of the forefoot since the bottom surface 96 of the last of the present invention is elevated along the medial side of the last.

FIG. 15B illustrates a cross section of the last 90 taken along line 15B—15B on the forefoot portion of the last shown in FIG. 15. As shown in FIG. 15B, the inner edge portion 98 of the bottom surface 96 of the last 90 slopes downwardly as described above. However, since the width of the inner edge portion 98 varies from the distal end to the proximate end of the forefoot portion of the last and since the height of the cavity along the medial side of the last is preferably uniform, the slope of the inner edge portion varies, also as described above with respect to the forefoot support system 60. As shown in FIG. 15B, the slope of the inner edge portion 98 of the bottom surface of the last is more gradual than the slope shown in FIG. 15A since the cross section taken along line 15B—15B is taken across a wider part of the inner edge portion 98 of the last.

In any of the above applications, it will be appreciated that the required amount of vertical support and the forefoot support system 60 varies depending upon the degree of Rothbart's foot structure present in an individual's forefoot. The amount of vertical support required is determined by using calibrated wedges.

Figure 17:
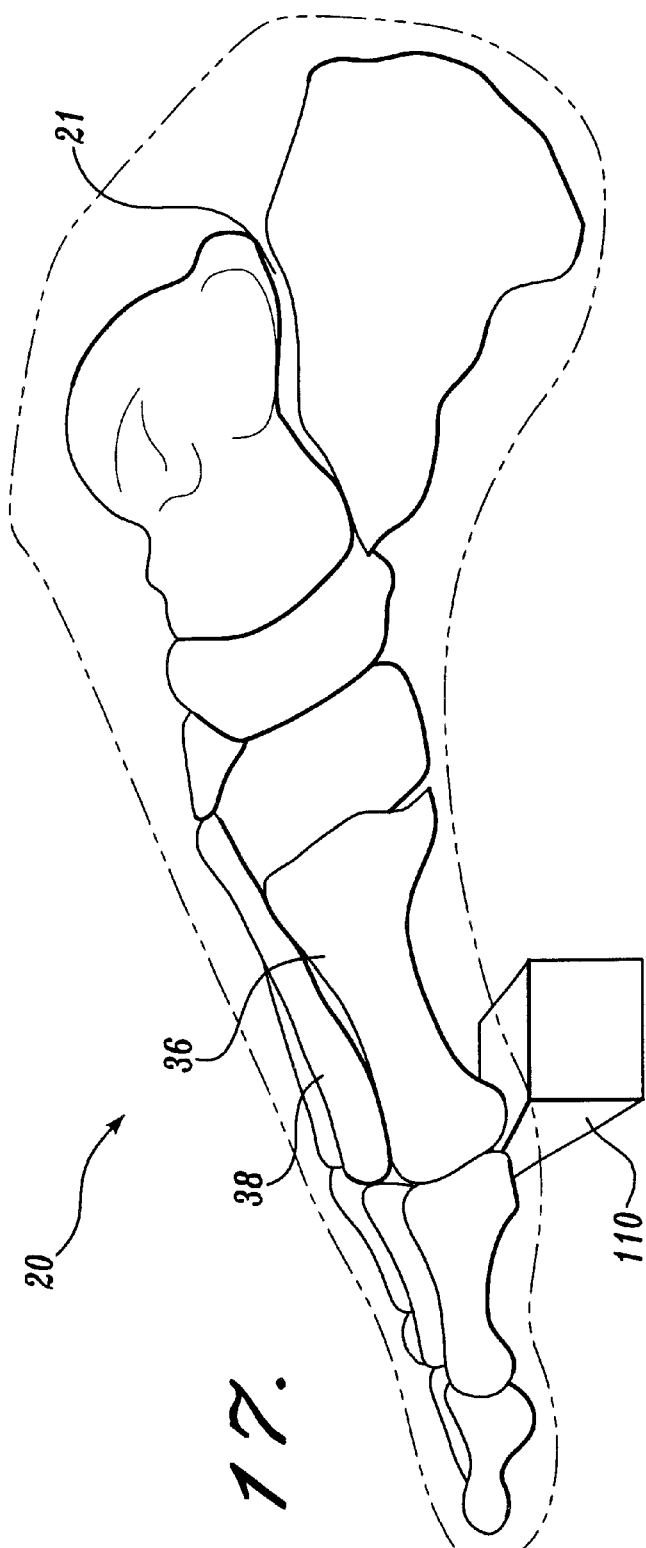
FIG. 17 is a side view of foot depicting a calibrated wedge underneath the medial column of the forefoot.

FIG. 17 illustrates a calibrated wedge 110 positioned under a forefoot 20. While an individual with Rothbart's Foot Structure is standing, the calibrated wedge 110 is slid underneath the distal end of the first metatarsal 36, but should not be slid underneath the second metatarsal. Incremental wedging is applied to the foot until the subtalar joint 21 remains in joint congruity as the individual's weight is transferred forward to the toes. This procedure emulates the transfer of forces in the forefoot during late stance phase of gait. The amount of vertical support required to achieve this, represents the amount of Rothbart's Foot Structure present in that forefoot.

A practitioner then determines the amount of vertical support required in a prescription. This force is described in terms of millimeters of vertical support. Typically, the practitioner's prescribed vertical support should be no more than 30% of what was measured in the forefoot so that the body does not react negatively to the positional shift. Thereafter, based upon medical discretion, the practitioner could increase the prescription with time. The vertical support necessary to support Rothbart's Foot Structure can vary from 2 mm to 70 mm.

Additionally, it will be appreciated that the precise dimensions of the forefoot support system could follow a predetermined generic dimension for mass production and distribution. It has been estimated that over 95% of the adult population has some degree of Rothbart's Foot Structure. Therefore, a forefoot support system with a minimal degree of vertical support can be mass produced. This mass production could best be achieved using a last incorporating the forefoot support system as described above.

As will be readily appreciated by those skilled in the art and others, a forefoot support system formed in accordance with the invention has a number of advantages. First, by supporting the medial column of a forefoot, exhibiting Rothbart's Foot Structure, from the hallux to the first metatarsal head, the forefoot support system effectively supports the forefoot in its anatomically neutral position both statically and dynamically while walking. In particular, the forefoot support system directs the forefoot to move in a linear fashion by preventing the forefoot from twisting and crashing into a shoe as weight is transferred forward over the forefoot. Specifically in this regard, the forefoot support system is active during the late stance of gait, or "toe-off," where prior orthotics or forefoot devices have proven inactive, since it supports the hallux as well as the rest of the medial column of the forefoot. Furthermore, when the forefoot is maintained in this position, such that Rothbart's Foot Structure is supported, the forefoot does not collapse into the shoe, and thus, walking becomes easier and more comfortable. Even further, the forefoot support system of the present invention reduces hyperpronation of the forefoot, and therefore, also reduces knee and lower back problems, such as knee-knocking and swaybacks, which are commonly associated with an unstable forefoot structure.

While the preferred embodiment of the invention has been illustrated and described, it will be appreciated that various changes can be made therein without departing from the spirit and scope of the invention. For instance, the degree of the slope of the forefoot support system and thus the height of the inner edge can vary for persons with more severe cases of hyperpronation and Rothbart's Foot Structure. Furthermore, the area of the forefoot support system can vary according to forefoot size. Even further, an arch support can be used in combination with the forefoot support system to provide additional support when necessary.

The embodiments of the invention in which an exclusive property or privilege is claimed are defined as follows:

1. A forefoot support system on which a forefoot rests, the forefoot having a medial side, a first toe, a first metatarsal, a second toe, a second metatarsal, the first toe and first metatarsal each having a lateral margin and the second toe and second metatarsal each having a medial margin, the forefoot support system comprising:

an elongate bed extending longitudinally along the first toe and a portion of the first metatarsal for supporting the forefoot;

the elongate bed having an inner edge extending along a contour of the medial side of the forefoot and an outer edge extending longitudinally in a zone substantially between the lateral margin of the first toe and first metatarsal and the medial margin of the second toe and second metatarsal; and the elongate bed decreasing in thickness from the inner edge to the outer edge, wherein the elongate bed provides support primarily to the first toe and the portion of the first metatarsal.

2. The forefoot support system of claim 1, wherein the first metatarsal has an anterior head, the elongate bed extends forwardly to an anterior end of the first toe and backwardly to a position proximal to the anterior head of the first metatarsal.

3. The forefoot support system of claim 2, wherein the forefoot support system is an orthotic.

4. The forefoot support system of claim 2, wherein the forefoot support system is integrated in a shoe bed of a shoe.

5. The forefoot support system of claim 1, further comprising a plate having a uniform thickness and shaped such that it follows the contour of the sole of the forefoot.

6. The forefoot support system of claim 5, wherein the plate is positioned underneath the elongate bed.

7. The forefoot support system of claim 5, wherein the plate is position on top of the elongate bed.

8. The forefoot support system of claim 5, wherein the plate and the elongate bed are an integrated unit.

9. The forefoot support system of claim 8, wherein the forefoot support system is an insole for a shoe.

10. The forefoot support system of claim 1, wherein the elongate bed linearly decreases in thickness from the inner edge to the outer edge.

11. The forefoot support system of claim 1, wherein the elongate bed decreases in thickness according to a concave slope line.

12. The forefoot support system of claim 1, wherein the elongate bed decreases in thickness according to a convex slope line.

13. The forefoot support system of claim 1, wherein the elongate bed decreases in thickness according to a stepped slope line.

14. The forefoot support system of claim 1, wherein the elongate bed does not significantly elevate the second toe and the second metatarsal.

15. The forefoot support system of claim 1, wherein the outer edge extends longitudinally along the lateral margin of the first toe and first metatarsal.

16. A method for supporting a hyperpronating forefoot, the forefoot having a sole, a medial side, a first toe, a first metatarsal, a second toe, a second metatarsal, the first toe and first metatarsal each having a lateral margin mad the second toe and second metatarsal each having a medial margin, the method comprising:

providing an elongate bed for supporting the sole of the forefoot along the medial side of the forefoot;

the elongate bed having an inner edge extending along a contour of the medial side of the forefoot and an outer edge extending longitudinally in a zone substantially between the lateral margin of the first toe and first metatarsal and the medial margin of the second toe and second metatarsal, and the elongate bed decreasing in thickness from the inner edge to the outer edge, wherein the elongate bed provides support primarily to the first toe and first metatarsal.

17. The method of claim 16, wherein the first metatarsal has an anterior head, the elongate bed extends from the first toe to a position proximal the anterior head of the first metatarsal.

18. The method of claim 16, wherein the elongate bed gradually decreases toward the distal end of the forefoot.

* * * * *

UNITED STATES PATENT AND TRADEMARK OFFICE
CERTIFICATE OF CORRECTION

PATENT NO. : 6,412,198 B1
DATED : July 2, 2002
INVENTOR(S) : B.A. Rothbart

It is certified that error appears in the above-identified patent and that said Letters Patent is hereby corrected as shown below:

Column 10,
Line 51, "position" should read -- positioned --

Column 11,
Line 10, "mad" should read -- and --

Column 12,
Line 4, "second metatarsal, and" should read -- second metatarsal; and --

Signed and Sealed this

Twenty-eighth Day of January, 2003

JAMES E. ROGAN
*Director of the United States Patent and Trademark Office*